(12) United States Patent
Jussel

(10) Patent No.: US 9,951,993 B2
(45) Date of Patent: Apr. 24, 2018

(54) DENTAL OVEN

(75) Inventor: Rudolf Jussel, Feldkrich-Gisingen (AT)

(73) Assignee: Ivoclar Vivadent AG, Schaan (LI)

( * ) Notice: Subject to any disclaimer, the term of this patent is extended or adjusted under 35 U.S.C. 154(b) by 753 days.

(21) Appl. No.: 13/555,540

(22) Filed: Jul. 23, 2012

(65) Prior Publication Data

US 2013/0029279 A1 Jan. 31, 2013

(30) Foreign Application Priority Data

Jul. 25, 2011 (EP) .................... 11175194

(51) Int. Cl.
*F27D 7/06* (2006.01)
*F27B 17/02* (2006.01)
*A61C 13/20* (2006.01)

(52) U.S. Cl.
CPC ........... *F27B 17/025* (2013.01); *A61C 13/20* (2013.01)

(58) Field of Classification Search
USPC ................. 432/23, 37, 200, 51, 25
See application file for complete search history.

(56) References Cited

U.S. PATENT DOCUMENTS

| 2,636,915 A * | 4/1953 | Gold ........................ A61C 13/20 |
| | | 126/273 R |
| 3,109,911 A * | 11/1963 | Kremer ....................... 219/390 |
| 3,694,122 A * | 9/1972 | MacDonald ............. F27D 11/02 |
| | | 425/171 |
| 3,786,164 A * | 1/1974 | Hintenberger ................. 219/393 |
| 3,909,590 A * | 9/1975 | Jensen .................... A61C 13/20 |
| | | 219/390 |
| 4,139,341 A * | 2/1979 | Pfaffenbauer ................. 432/184 |
| 4,445,012 A * | 4/1984 | Blackburn ............... A61B 5/08 |
| | | 128/205.12 |
| 5,086,824 A * | 2/1992 | Tsuda ..................... B22D 17/32 |
| | | 164/151.1 |
| 5,219,409 A * | 6/1993 | Campbell ............... B22D 17/32 |
| | | 164/113 |
| 5,225,142 A * | 7/1993 | Heilmann ............... C21D 1/767 |
| | | 266/250 |
| 5,379,826 A * | 1/1995 | Miwa et al. .................... 164/4.1 |
| 5,432,319 A | 7/1995 | Indig |
| 2010/0212588 A1* | 8/2010 | Suda ....................... C30B 29/06 |
| | | 118/663 |

FOREIGN PATENT DOCUMENTS

| DE | 1160777 A | 7/1964 |
| DE | 3927998 A1 | 3/1990 |
| DE | 4002358 C1 | 10/1991 |

* cited by examiner

*Primary Examiner* — Nathaniel Herzfeld
(74) *Attorney, Agent, or Firm* — Ann M. Knab; Thad McMurray

(57) ABSTRACT

A dental oven comprising a firing chamber for the heat treatment of dental restoration parts. The firing chamber is connected to a negative pressure source via a suction line. A valve arrangement is located between the firing chamber and the suction line with the aid of which the suction line is closable towards the firing chamber in order to maintain a negative pressure in the firing chamber. The suction line between the valve arrangement and the negative pressure source is ventilatable via an ambient air connection.

15 Claims, 2 Drawing Sheets

DENTAL OVEN

CROSS-REFERENCE TO RELATED APPLICATIONS

This application claims the benefit of European Application No. 11175194.7 filed Jul. 25, 2011, which is hereby incorporated by reference in its entirety.

TECHNICAL FIELD

The present invention relates to a dental oven and to a method of operating a dental oven.

BACKGROUND

Dental ovens which fire dental restoration parts in firing cycles have been known for a long time. Thus, DE 1 160 777 A discloses an electrically heatable dental oven comprising a negative pressure source in the form of a piston pump as a negative pressure pump. As the pump, depending on its design, causes a significant level of operating noise, it is preferably operated via a negative pressure or suction line which is several meters long, i.e., it is spatially separated slightly from the dental oven. Hereby, the suction line is appropriately formed as a hose which is resistant to negative pressure and flexible to a certain extent. In addition, this hose must be resistant to temperatures as the air which is released by the firing chamber of the dental oven may be relatively hot, although it is being cooled when passing through the wall of the oven.

Typically, thermal stability of up to 300° C. must be given, in fact as a first approximation independently of the fact if the dental oven is operated at a firing temperature of e.g., 1200° C. or at a relatively high firing temperature of 1600° C.

Recently, "muffle ovens" have been used as dental ovens for the production of dental restoration parts. An example of this is disclosed in DE 40 02 358 C1. In such dental ovens, the ceramic part to be shaped/produced is introduced as a blank or "green body" into a sprue which is formed in a prepared muffle made of gypsum. The muffle is heated together with the dental restoration part, in fact, in most cases, after it has already been heated to a starting temperature of e.g., 700° C. in a "pre-heating furnace". The firing chamber of this dental oven is put under negative pressure by a negative pressure pump which produces negative pressure, i.e., a so-called "vacuum". Subsequently, a press plunger presses the blank and upon softening of the dental restoration material due to the increasing temperature, the restoration material, favored by the negative pressure which exists in the entire firing chamber, reaches the mold cavities in a pore-free manner whose shape corresponds to that of the dental restoration parts to be produced.

This method has been known for a long time and has stood the test of time, whereas, of course, a condition for the successful provision of the dental restoration parts is that enough negative pressure exists in the entire firing chamber, i.e., also in the muffle itself.

Gypsum or similar casting compounds are not gas-tight, nor liquid-tight, but have a certain degree of flow resistance so that the formation of a completely balanced negative pressure in the firing chamber requires an operation of the suction pump, which forms the negative pressure source, of at least several seconds or minutes. Especially with pre-heated muffles, the "starting temperature" is then already significantly higher than the room temperature, and hot air flows into the suction line immediately when the suction pump is turned on.

In order to prevent the suction pump from being damaged by the hot air, which may also be contaminated, the manufacturers at least of the pumps, or maybe also the manufacturers of the dental ovens, stipulate that the negative pressure line must not be shorter than a certain length, e.g., 3 meters. In order to ensure the desired flexibility of the negative pressure line, the inner diameter, thus the outer diameter, is limited to measurements which are favorable for production and which also make possible the use of standard negative pressure lines. The length of such negative pressure lines can also be adapted to the spacial circumstances in the dental laboratory, as they are available in the piece.

A further advantage of the slightly longer suction line is that a certain "pressure elasticity" is provided; the negative pressure line acts as a buffer and at the same time prevents negative pressure peaks which can be introduced by the negative pressure pump depending on its construction.

A serious disadvantage which up to now, however, prevented the desired design of a negative pressure line in any desired length was and is the tendency of these lines to clog. Due to the large temperature gradient between the firing chamber and the ambient air, the humidity from the firing chamber, which is not carried along, condenses in the negative pressure line. This not only leads to an increase in flow resistance but in particular also to a worsening of the quality of the negative pressure, as the evaporation temperature of the water droplets in the negative pressure line decreases as the negative pressure increases.

In view of this fact, the manufacturers of dental ovens have regularly realized special dehumidification programs which make various attempts to remove the water droplets located in the negative pressure lines.

It has also been suggested to provide several negative pressure lines without further ado and to simply exchange them when the formation of droplets is too high. But this is impractical and requires additional storage, and it may also result in sealing problems when re-assembling the fresh negative pressure line.

It has been known for a longer period of time that the muffle itself and/or the dental restoration material which consists of dental ceramics can be exposed to a considerable degree of residual humidity.

In order to remove the residual humidity, the dental oven is operated at a dehumidification temperature under negative pressure. During this dehumidification program the valves of the dental oven are opened towards the external negative pressure source so that air which is enriched with water vapor flows through the suction line to the negative pressure source. By doing this, the suction line is excessively soaked. This can be problematic for the dental ceramics which are subsequently heated and for the negative pressure, which must be maintained in the desired quality during the pressing process.

When the deposition of moisture is too high in the long suction line, it does not function anymore, which has a negative impact on the quality of the restoration.

SUMMARY

The present invention is based on the task of creating a dental oven and a method for operating a dental oven wherein the quality of the dental restoration parts are improved without requiring particular investment in dental ovens.

This task is inventively solved by the attached claims, which are herein incorporated by reference.

According to an embodiment of the invention the provision of a specific flushing program for the suction line or the negative pressure line is especially favorable which cleans the line, on the one hand, i.e., brings back the flow resistance to the original degree, and also removes the existing moisture in the form of water droplets, on the other hand. During this flushing program the negative pressure in the firing chamber is maintained and this occurs by means of the valve arrangement, which is provided at or in the dental oven.

Accordingly, the inventive flushing program can be carried out even during the above dehumidification program of the dental oven, but also at any other point in time, i.e., also during the firing process, or when the firing oven is turned off or during the negative pressure test program.

According to an embodiment of the present invention, it is especially favorable that the cold suction hose which forms the suction line can be completely flushed and dehumidified. In the area of the firing oven itself, i.e., between the valve arrangement and the firing chamber, the suction hose or suction line is comparatively hot so that no deposition occurs there. When the suction hose leaves the dental oven it is subject to the ambient temperature which forms a cold trap for the hot and moist air in the suction line which leads to a deposition of water droplets.

According to an embodiment of the invention it is favorable that cost-effective negative pressure pumps can also be used, including pumps which do not allow a re-start of the negative pressure pump under negative pressure. In order to restart such a pump, it can be switched to flushing, temporarily and without further ado, so that the pump can re-start. However, during the renewed re-starting of the pump, the negative pressure in the firing chamber is maintained.

According to an embodiment of the invention it is especially favorable that the elements of the negative pressure source and the suction hose, which extend outside of the dental oven, can be completely separated via the valve arrangement which seals the firing chamber. By decoupling it in terms of pressure, maintenance work can be carried out without any delay, e.g., exchanging the pump, while the negative pressure in the firing chamber is maintained. It is also to be understood that, in this way, a re-start of the negative pressure pump is possible without any delay.

According to an embodiment of the invention it is also favorable to do without pumps with integrated free-wheeling which are comparatively expensive. Such vacuum pumps which have already been suggested make possible a flushing of the pump itself without affecting a negative pressure line so that the inventive advantages could not be achieved with such types of pumps.

According to an embodiment of the invention it is provided, compared to this, that especially the suction line or the negative pressure line, which as the cold trap is particularly subject to condensing, can be cleaned using a pump or can be flushed. At a pump capacity of between 14 liters per minute and 20 liters per minute, in slightly more than one minute 1 Mol of water can be removed from the suction line, so that a short interruption of the pumping force to the firing chamber, wherein, however, the negative pressure is maintained in the firing chamber, is enough in most cases to ensure the desired flushing.

In a further advantageous embodiment a control device is used for the valve arrangement which turns on manually or automatically the valve(s) in order to achieve the aforementioned purpose. An on-/off-valve can, for instance, be used for the flushing program, which extends between the suction line and the firing chamber and which is closed when the flushing program is to be started. Adjacent to this valve, i.e., at the front part of the suction line, a further on-/off-valve is provided in this embodiment which also forms part of the valve arrangement and which then connects the suction line input with a flushing input. The flushing input can be connected to the ambient air, preferably via an air filter, which keeps away pollutants in the ambient air from the suction line.

Instead of using two on-/off-valves, a sole switching valve may be used which offers the same function, and practically switches the suction line input between both the connections "ambient air" and firing "chamber".

The firing chamber connection can be directly (i.e., naturally sealed) flange-mounted to the envelope of the firing chamber which consists of metal. Typically, the insulation material is relatively porous so that a separate line which passes through the insulation material is unnecessary. Moreover, the porous insulation material, e.g., lightweight refractory bricks, serves as an additional input filter for the suction line.

In an alternative embodiment the insulation material at the suction input is provided with a special filter element which is replaceable. The exhaust air of the firing chamber then flows through this filter element so that chemical pollutants can be possibly trapped already at the filter. Depending on the design, this filter element may serve as thermal insulation at the same time so that, compared to lightweight refractory bricks, no additional heat losses occur. If necessary, the filter element can also be provided with a catalyst for chemical compounds which can be catalyzed.

When using fiber material as a thermal insulation material, which is typically more hygroscopic than lightweight refractory bricks, the suction connection can be attached to the wall of the oven, as the thermal insulation material is heated relatively strongly even if it is formed in a filamentary way so that no moisture depositions occur.

Between the envelope of the firing chamber and the housing of the dental oven, the valve arrangement and the respective control device are provided, according to an embodiment of the present invention. Even at a firing chamber temperature of 1,600° C., the valve arrangement cannot overheat in this embodiment. It is typically spaced apart from the wall of the firing chamber via a short piece of pipe, and is cooled by the ambient air.

According an embodiment of the present invention, an inventive dental oven can also be realized through retrofitting, e.g., by adding only one additional valve or by changing the control.

According to an embodiment of the invention it is also possible to record the interior pressure of the firing chamber via the control device and to use the measurement signal obtained for turning on the flushing program. In this way, a flushing program can be automatically added when it is determined during the generation of negative pressure in the firing chamber that the interior pressure in the firing chamber is decreasing too slowly, i.e., when the pump does not produce enough effective power, as the suction line is clogged, and water droplets have condensed there.

The measuring of the negative pressure can either take place at the same connection of the envelope of the firing chamber, as mentioned before, or, if necessary, also at a separate measuring connection.

In a modified embodiment, two suction connections are realized at the envelope of the firing chamber to which negative pressure can be applied separately. Switching can, for instance, be realized using a switching valve, which is provided for this purpose, and it is also possible to realize one of the connections at the bottom part of the oven and the other connection at the top part of the oven or the oven head.

In an advantageous development of the invention the control device for the valve arrangement vents the suction line for a predetermined period of time, such as for 1 minute, by selecting ventilation program, and carries out the flushing program, which may be conducted in recurring cycles.

In an advantageous development of the invention the valve arrangement is provided with a switching valve with an output connection connected to the suction line and wherein one switching connection is the ambient air connection and wherein another switching connection is the firing chamber suction connection, and that the switching valve is controllable by the control device.

In an advantageous development of the invention the control device of the dental oven also acts on the negative pressure source, which is provided in particular with a negative pressure pump, and that the negative pressure source is connected to the control device via a control line or wirelessly for turning it on and off, and that the control device turns on in particular the negative pressure source when the suction line is supposed to be ventilated.

In an advantageous development of the invention the valve arrangement is provided with a valve, via which, upon its opening, the firing chamber connection of the valve arrangement can be connected to the ambient air, and that in particular the control device of the dental oven turns off the negative pressure source in this state of the valve arrangement.

In an advantageous development of the invention a negative pressure sensor is connected to the firing chamber and measures the pressure or the negative pressure in the firing chamber, which output signal is recorded by the control device of the dental oven, wherein the control device controls the desired negative pressure in the firing chamber by turning on the negative pressure source.

In an advantageous development of the invention the negative pressure in the firing chamber is recorded continuously and the negative pressure source is turned on when the negative pressure is too low, in particular, if in spite of a turning on of the negative pressure source, the negative pressure does not increase sufficiently, the valve arrangement is controlled and the flushing program is turned on.

In an advantageous development of the invention the flushing program is turned on during a firing cycle, during a specific service program of the dental oven or between firing cycles.

In an advantageous development of the invention the control device records the output signal of the negative pressure sensor of the dental oven continuously or recurrently and records the pressure drop gradient, i.e., the drop in pressure per unit of time, while the negative pressure source is turned on, and turns on the flushing program when the pressure drop gradient falls below a predetermined threshold value.

In an advantageous development of the invention the firing chamber of the dental oven is connected to the negative pressure source via a second suction line, and both suction lines can be turned on optionally via a switching valve so that at any time one of the suction lines is turned on and the other is closed.

In an advantageous development of the invention a dental oven known per se can be retrofitted with a valve arrangement comprising at least two valves or at least one switching valve with a control device, which allows for a flushing program according to any of the foregoing claims.

In an advantageous development of a method of the invention when the negative pressure source is turned on, i.e., via the valve arrangement interconnected suction line, the development of the negative pressure in the firing chamber is measured continuously or periodically recurrently and that a flushing program is started when the negative pressure in the firing chamber decreases more slowly than in correspondence with a predetermined threshold value.

BRIEF DESCRIPTION OF THE DRAWINGS

Embodiments of the present invention will be more fully understood and appreciated by the following Detailed Description in conjunction with the accompanying drawings, in which.

DETAILED DESCRIPTION

Figure 1:
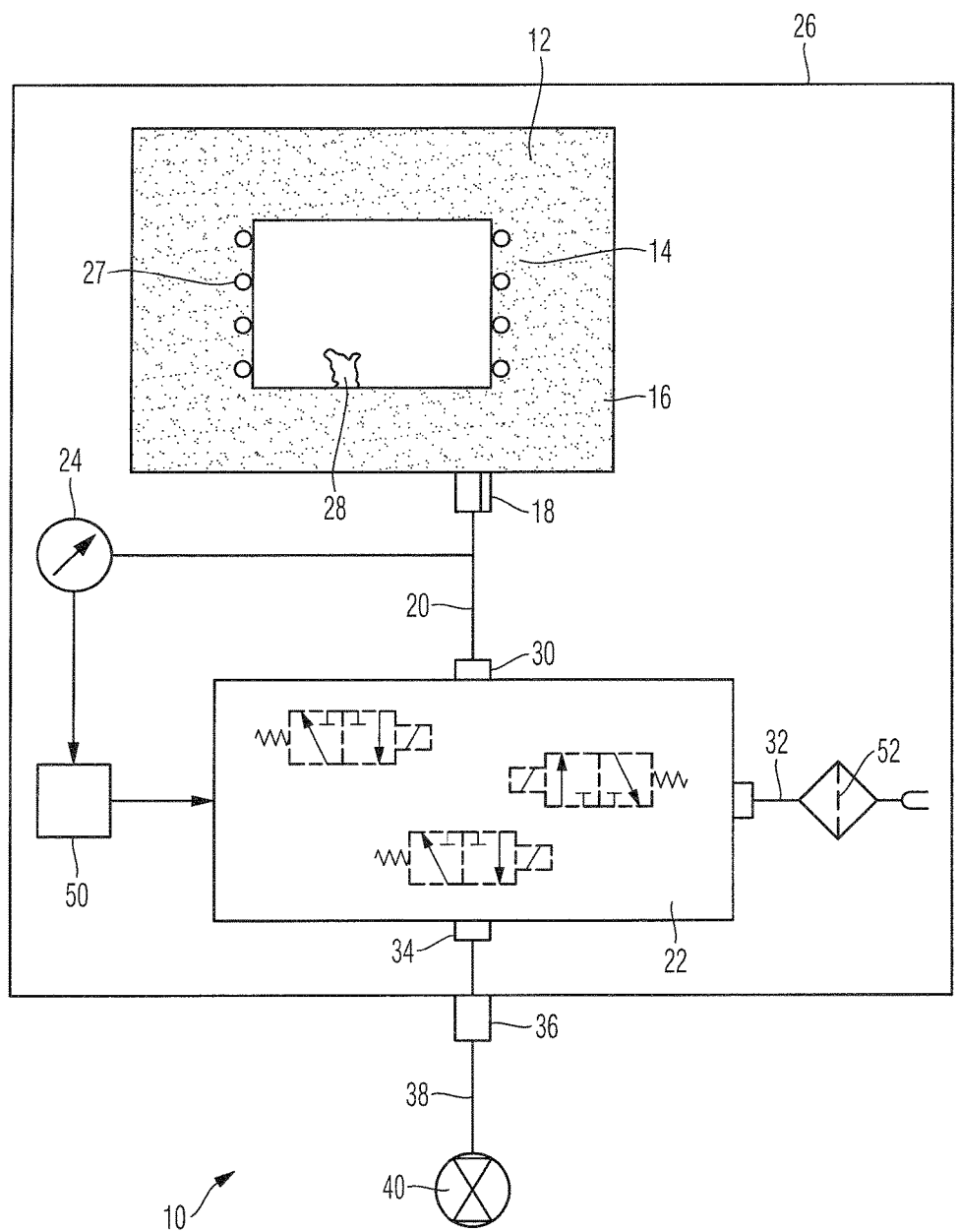
FIG. 1 shows a schematic view of an inventive dental oven in a first embodiment.
Figure 2:
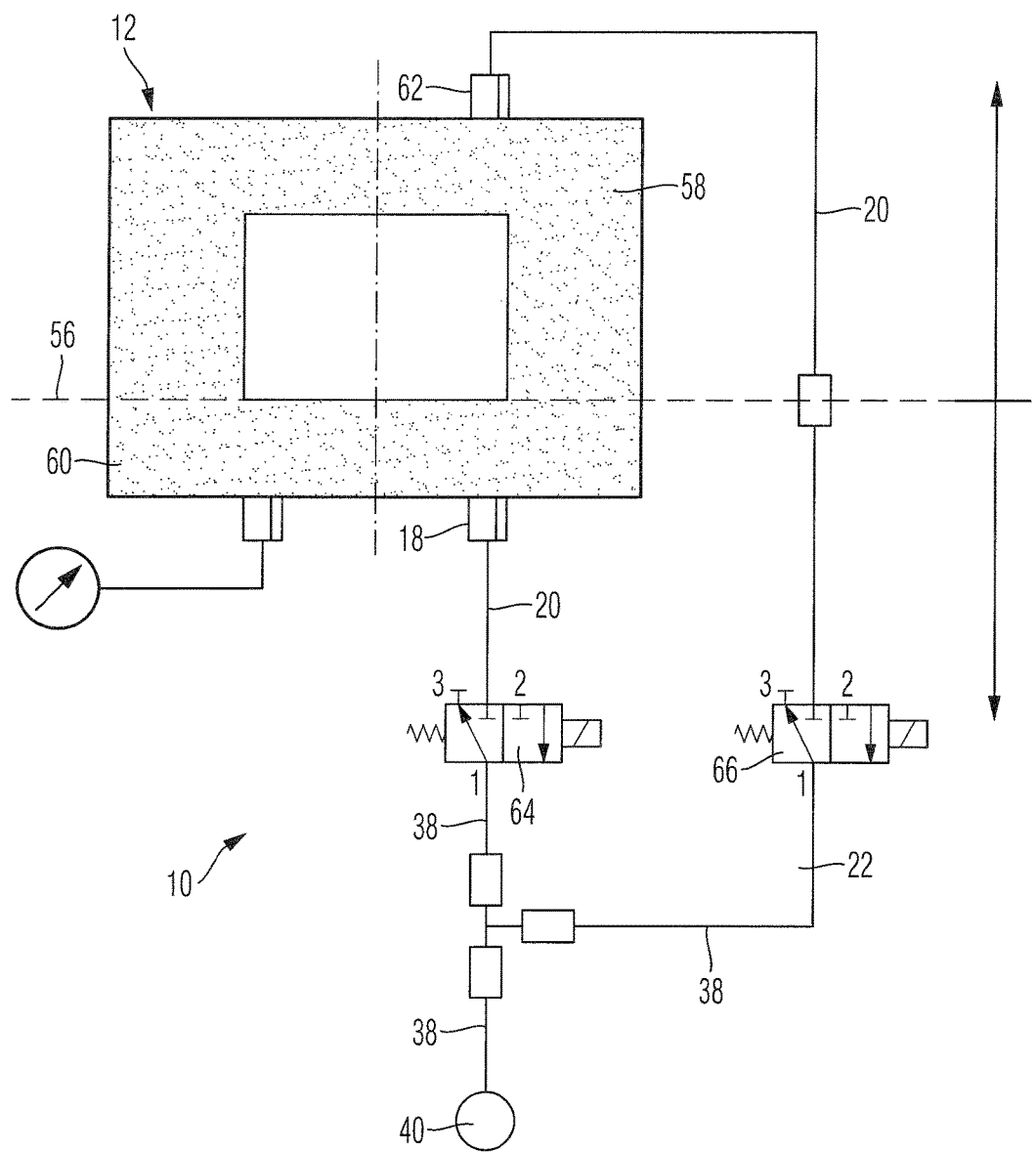
FIG. 2 shows a schematic view of an inventive dental oven in a second embodiment.

The dental oven 10 illustrated in FIG. 1 is provided with a firing chamber 12 which is intended for the heat treatment of dental restoration parts. The firing chamber can be opened, either using a door or via a division between the bottom of the firing chamber and the oven head, which is schematically illustrated in FIG. 2, or in other ways, known in the art.

The firing chamber 12 is sealed with respect to the environment. It is lined with thermal insulation material 14 which is provided with relatively thick walls in a way known, in order to ensure a good degree of thermal insulation. The thermal insulation material is permeable to gases in a way known and is surrounded by a firing chamber envelope 16 which is gas-tight.

The envelope of the firing chamber is provided with a suction line connection 18, which is connected to a suction line in the form of a suction pipe. The suction pipe forms a connection between the envelope or periphery of the firing chamber 16 and a valve arrangement 22 whose function will be described in detail later.

Moreover, from the suction pipe 20 a stub is directed to a pressure gauge 24. The pressure gauge 24 or negative pressure gauge measures insofar via the suction pipe 20 the pressure in the interior of the firing chamber 12. The suction pipe 20 is provided with a relatively high thermal stability and is relatively short, e.g., 5 cm to 20 cm. It is connected to the valve arrangement 22 whose function will be described in detail later.

The firing chamber 12, the pressure gauge 24 and the valve arrangement 22, inclusive of the respective line connections, are entirely included in a housing 26 of the dental oven 10. The firing chamber 12 is provided with a heating unit 27 which is intended for the heating of the dental restoration part 28 which is accommodated in the firing chamber 12. In spite of the relatively thick thermal insulation material 14, a slight heating of the interior of the housing 26, when the heating unit 27 is turned on, cannot be prevented. This also holds true for the suction pipe 20 and, to a certain extent, for the valve arrangement 22 which are also located in the housing 26. However, the temperature decreases with an increasing distance to the firing chamber 12. But still the valve arrangement 22 can heat up to, for instance, more than 100° C. when the firing chamber 12 is heated to 1,600° C. for a longer period of time. This is why the valve arrangement 22 is built in a temperature resistant way so that it works without any problems, for instance even at temperatures of 200° C.

The valve arrangement 22 is provided with a firing chamber suction line connection 30, an ambient air connection 32 and an output connection 34 which is connected in the form of a flow connection via a flange 36 with a suction line 38. The suction line 38 is several meters long, for example, 2 m to 10 m. That end of the line, which does not face the housing 26, is provided with a piston pump 40 which acts as a negative pressure source.

It is to be understood that, in lieu of a piston pump, a membrane pump or any other pump can be used without further delay or complications. The pump does not have to have any specific degree of thermal stability due to the length of the suction line 38, which is subject to the ambient temperature and due to being uninsulated, the air which is sucked from the firing chamber 12 cools significantly, e.g., to 50° C., and practically every pump which is used for this purpose can tolerate such circumstances.

Subsequently, the function of the valve arrangement 22 is described.

At the beginning of a firing cycle the piston pump 40 is not turned on and the valve arrangement 22 establishes a connection between the firing chamber suction line connection 30 and the output connection 34. The ambient air connection 32, however, is locked.

In this state, the firing chamber 12 is under atmospheric pressure and can be opened and closed in any desired way in order to introduce the dental restoration part 28. Preferably, the dental restoration part 28 is received by a preheated muffle which is not illustrated, and the dental oven 10 is formed as a press oven. It is to be understood that an oven which is solely used for firing can be alternatively realized in which the dental restoration part is fired immediately.

In order to start the firing cycle, the heating unit 27 is turned on and at the same time the piston pump 40. In this state, the valve arrangement 22 is also connected between firing chamber suction line connection 30 and output connection 34 so that hot air is increasingly pumped out of the firing chamber 12 and gradually negative pressure is generated.

Typically, muffles and dental restoration parts are provided with a certain degree of residual humidity. In case this degree of residual humidity is not really low, a so-called dehumidification program is used regularly before the actual firing cycle is started, and this program serves to remove the humidity. For this purpose, the heating unit is turned on in such a way that the temperature in the interior of the firing chamber 12 amounts to, e.g., 140° C. The air which is enriched with water vapor is drained and reaches the outside through the piston pump 40.

As the suction line 38 is, however, markedly cooler than 100° C., at least at the end which faces the piston pump, the contained moisture condenses and forms droplets in the interior of the suction line 38. On the one hand, these droplets constrict the cross sectional area of flow so that the flow resistance increases. On the other hand, they affect, which is even worse, the quality of the produced negative pressure. The reason for this is that the evaporation temperature of water decreases considerably when the pressure decreases, i.e., when the vacuum increases, so that the water droplets evaporate gradually and the water vapor which is produced in this way is removed instead of the air which is to be evacuated.

When the dehumidification program is finished, typically, the actual firing cycle is carried out at an increased temperature, while at the same time the piston pump 40 is in operation and the pressure in the firing chamber 12 continues to decrease accordingly. The actual firing temperature typically amounts to considerably more than 1000° C., for instance approximately 1150° C. for a lithium disilicate ceramic or 1600° C. for a zirconium dioxide ceramic.

During the heating phase of the firing cycle, the pressure in the interior of the firing chamber 12 which is measured by the pressure gauge 24 is supposed to decrease further. This is recorded by the pressure gauge 24. As long as the decrease of the pressure in the firing chamber is carried out in a way which corresponds to the rated power of the piston pump 40, the valve arrangement 22 remains in the aforementioned position.

The pressure gauge 24 is connected to a control device 50 which evaluates the output signal of the pressure gauge 24. The control device 50 electrically controls the valve arrangement 22. If the control device 50 determines that the pressure gradient is too low, i.e., when the pressure in the firing chamber 12 drops too slowly, the control device 50 switches the valve arrangement 22. In this connection, an inventive flushing program is carried out. In this state of the valve arrangement 22 the firing chamber suction line connection 30 is locked.

However, in this state a connection between the ambient air connection 32 and the output connection 34 exists. Ambient air is drawn via an air filter 52. In this state, i.e., during the flushing program, the piston pump 40 operates at its highest pump capacity of e.g., 20 liters per minute. The flow rate in the suction line 38 is correspondingly high. Because of this and because of the dry ambient air which enters the suction line 38, the suction line 38 is flushed. The flushing program is carried out until the interior of the suction line 38 is dry, for instance for several minutes. As an alternative, the speed of the piston pump 40 can also be recorded, and the flushing program can be stopped when the speed of the piston pump 40 shows that the suction line 38 has been flushed completely.

In that case, the drawing of air from the firing chamber 12 is continued. As the firing chamber suction line connection 30 has been locked in the meantime, the negative pressure which has been generated is not lost and the pressure is again further lowered at full power of the piston pump 40, i.e., without being hindered by a clogged suction line 38.

The function of the valve arrangement 22 corresponds to that of a switching valve. In order to maintain the negative pressure in the firing chamber 12, it is, however, favorable when the switching from the flushing position to the normal position of the valve arrangement is delayed to such an extent that the ambient air connection is first locked and the suction line connection 30 is only opened when the piston pump 40 has also put the several meter long suction line 38 and the output connection 34 under a suitable negative pressure.

Otherwise, it can be expected that the air which is in the suction line 38 due to the flushing program flows into the firing chamber 12 rearward as the piston pump 40 cannot build up the negative pressure fast enough again.

It is more favorable if the "switching valve" of the valve arrangement 22 consists of two individual valves which are controlled by the control device 50 in the aforementioned manner.

Therefore, a flushing program can inventively be carried out at any time. Basically, this is also possible during a dehumidification program but preferably when the actual firing cycle is started with the firing program in order to remove the moisture, which originates from the dehumidification program, from the suction line 38 in advance.

However, it is also possible to carry out the flushing program during a specific service program of the dental oven, or in between firing cycles, i.e. when the dental oven 10 is open anyway.

FIG. 2 shows a modified embodiment of an inventive dental oven 10. Same or corresponding elements as in FIG. 1 are provided with the same reference numbers in this embodiment.

As can be seen from FIG. 2, the dental oven 10 is provided with a divisional plane 56 with regard to its firing chamber 12. At the divisional plane an oven head 58, which is also referred to as oven top, can be separated from an oven bottom 60. This happens by either lifting the oven head 58 or by tilting it upwards at a slight angle, while the oven bottom 60 remains stationary. This embodiment is preferred as the dental restoration parts which are located in the firing chamber 12 are not subjected to any vibrations. Alternatively, it is also possible that the oven top 58 remains stationary while the oven bottom 60 is moved downward. This design can be produced more cheaply as the heating unit 27 can also remain stationary.

It is to be understood that in both cases the divisional plane 56 needs to be sealed sufficiently.

In this design example, the firing chamber 12 is provided with two suction connections 18 and 62 whereas the suction connection 62 is attached at the oven head 58 and the suction connection 18 at the oven bottom 60.

Both suction connections lead to the valve arrangement 22 via suction pipes 20. The valve arrangement 22 is provided with a first three-/two-way valve 64 and a second three-/two-way valve 66. Even if the valve 66 shows a considerable distance to the suction connection, it is to be understood that in practice only one short suction pipe 20 is provided there. Downstream of every valve 64 and 66 the suction line 38 is connected which extends over several meters each to the piston pump 40.

It is to be understood that, for this purpose, the output suction lines 38 of the valves 64 and 66 are brought together in a way known in the art.

The valves 64 and 66 are switchable independently of each other in any desired way by the control unit 50 which is not illustrated. They are connected in such a way that ambient air can be drawn via the suction lines 38 alternatingly, so that a switching can be carried out without further delay or complications if the suction line 38 which has been used up to this point in time is clogged.

This embodiment has the advantage that flushing programs can be carried out less frequently since one of the suction lines 38 is available as a spare line. For example, the dehumidification program can be realized via the suction connection 62, i.e., at an interconnected valve 66. As soon as the dehumidification program has been finished, the valve 66 will be closed. For the time being, the respective line 38 which will then be rather humid remains as it is, and the valve 64 will be closed. The suction line 38 which extends from the valve 64 to the pump 40 is not clogged yet so that the negative pressure can be produced in the firing chamber 12 at full pump capacity.

After having finished the actual firing cycle, both suction lines 38 and 62 can then be cleaned using flushing programs so that they are available for the next firing cycle.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. Dental oven comprising
   a firing chamber for the heat treatment of dental restoration parts, the firing chamber connected to a negative pressure source via a suction line,
   wherein a valve arrangement is disposed between the firing chamber and the suction line,
   wherein the suction line is closable towards the firing chamber in order to maintain a negative pressure in the firing chamber,
   wherein a pressure gauge measures pressure in the firing chamber,
   wherein the suction line comprises a flexible, uninsulated hose located between the valve arrangement and the negative pressure source and is ventilatable via an ambient air connection;
   wherein a control device is provided for the valve arrangement which is used to turn on a flushing program in which the valve arrangement locks a firing chamber suction line connection and connects the ambient air connection to the suction line and in which the negative pressure source draws ambient air through the suction line;
   wherein the flushing program can be carried out at any time; and
   wherein the control device is configured to evaluate an output signal of the pressure gauge, and if the control device determines the pressure gradient is too low, the control device switches the valve arrangement to start the flushing program.

2. Dental oven according to claim 1,
   wherein the control device for the valve arrangement vents the suction line for a predetermined period of time by selecting a ventilation program, and carries out the flushing program.

3. Dental over according to claim 2,
   wherein the predetermined period of time is 1 minute and the flushing program is carried out in occurring cycles.

4. Dental oven according to claim 1,
   wherein the valve arrangement is provided with a switching valve having an output connection connected to the suction line and having a first switching connection comprising the ambient air connection and having a second switching connection comprising the firing chamber suction connection, and
   wherein the switching valve is controllable by the control device.

5. Dental oven according to claim 1,
   wherein the control device of the dental oven also acts on the negative pressure source, the negative pressure source provided with a negative pressure pump, and
   wherein the negative pressure source is connected to the control device via a control line or wirelessly for turning the negative pressure source on and off, and
   wherein the control device turns on the negative pressure source when the suction line is to be ventilated.

6. Dental oven according to claim 1,
   wherein the valve arrangement comprises a valve, whereupon opening of the valve, the firing chamber connection of the valve arrangement can be connected to the ambient air, and
   wherein the control device of the dental oven turns off the negative pressure source in the valve arrangement.

7. Dental oven according to claim 1,
wherein a negative pressure sensor is connected to the firing chamber and measures the pressure or the negative pressure in the firing chamber, and
wherein an output signal of the negative pressure sensor is recorded by the control device of the dental oven, and
wherein the control device controls the desired negative pressure in the firing chamber by turning on the negative pressure source.

8. Dental oven according to claim 1,
wherein the negative pressure in the firing chamber is recorded continuously and
wherein the negative pressure source is turned on when the negative pressure is too low,
wherein, if turning on of the negative pressure source, the negative pressure does not increase sufficiently, the valve arrangement is controlled and the flushing program is turned on.

9. Dental oven according to claim 1,
wherein the flushing program is turned on during a firing cycle, during a specific service program of the dental oven, or between firing cycles.

10. Dental oven according to claim 1,
wherein the control device records the output signal of the negative pressure sensor of the dental oven continuously or recurrently and records the pressure drop gradient while the negative pressure source is turned on, and turns on the flushing program when the pressure drop gradient falls below a predetermined threshold value.

11. Dental oven according to claim 1,
wherein the pressure drop gradient comprises the drop in pressure per unit of time.

12. Dental oven according to claim 1,
wherein the firing chamber of the dental oven is connected to the negative pressure source via a second suction line, and that both suction lines can be turned on optionally via a switching valve so that at any time one of the suction lines is turned on and the other is closed.

13. Dental oven according to claim 1,
wherein a dental oven can be retrofitted with a valve arrangement comprising at least two valves or at least one switching valve with a control device, which allows for a flushing program.

14. Method for operating a dental oven in which dental restoration parts are heat-treated and put under negative pressure,
wherein the dental oven comprises a suction line comprising a flexible, uninsulated hose that extends between a firing chamber and a negative pressure source,
wherein the negative pressure can be produced in the firing chamber, a valve arrangement provided between the firing chamber and the suction line, the valve arrangement closes the suction line towards the firing chamber in order to maintain a negative pressure in the firing chamber, and the suction line between the valve arrangement and the negative pressure source is ventilated, via an ambient air connection;
wherein a control device for the valve arrangement turns on a flushing program in which the valve arrangement makes a connection between an output connection of the valve arrangement and the ambient air, via which the suction line can be flushed, wherein the negative pressure source draws in air through the suction line and wherein at the same time the valve arrangement locks the connection of the valve arrangement to the firing chamber;
wherein the flushing program can be carried out at any time; and
wherein the control device is configured to evaluate an output signal of the pressure gauge, and if the control device determines the pressure gradient is too low, the control device switches the valve arrangement to start the flushing program.

15. Method according to claim 14,
wherein when the negative pressure source is turned on via the valve arrangement interconnected suction line, the development of the negative pressure in the firing chamber is measured continuously or periodically recurrently and
wherein a flushing program is started when the negative pressure in the firing chamber decreases more slowly than in correspondence with a predetermined threshold value.

* * * * *